(12) United States Patent  (10) Patent No.: US 6,506,150 B1
Ouchi  (45) Date of Patent: Jan. 14, 2003

(54) SELF-RETAINING ENDOSCOPE

(75) Inventor: Teruo Ouchi, Saitama (JP)

(73) Assignee: Pentax Corporation, Tokyo (JP)

( * ) Notice: Subject to any disclaimer, the term of this patent is extended or adjusted under 35 U.S.C. 154(b) by 0 days.

(21) Appl. No.: 09/547,677

(22) Filed: Apr. 12, 2000

(30) Foreign Application Priority Data

Apr. 13, 1999 (JP) .......................................... 11-104795

(51) Int. Cl.[7] .............................................. A61B 1/005
(52) U.S. Cl. ...................... 600/132; 600/128; 600/146; 600/156; 600/139
(58) Field of Search ................................ 600/120, 132, 600/143, 139, 130, 131, 128, 151, 146, 156

(56) References Cited

U.S. PATENT DOCUMENTS

| | | | |
|---|---|---|---|
| 4,756,303 A | * 7/1988 | Kawashima et al. | 600/139 |
| 4,884,133 A | * 11/1989 | Kanno et al. | 348/68 |
| 4,977,886 A | * 12/1990 | Takehana et al. | 600/151 |
| 5,197,457 A | * 3/1993 | Adair | 600/104 |
| 5,411,020 A | * 5/1995 | Ito | 600/104 |
| 5,494,483 A | * 2/1996 | Adair | 348/45 |
| 5,531,664 A | * 7/1996 | Adachi et al. | 600/149 |
| 5,897,488 A | * 4/1999 | Ueda | 600/143 |
| 6,036,636 A | * 3/2000 | Motoki et al. | 600/141 |
| 6,086,528 A | * 7/2000 | Adair | 600/104 |
| 6,322,498 B1 | * 11/2001 | Gravenstein et al. | 600/120 |

FOREIGN PATENT DOCUMENTS

| | | |
|---|---|---|
| JP | 64-4450 | 1/1989 |
| JP | 64-76822 | 3/1989 |
| JP | 3-9705 | 1/1991 |
| JP | 6-114064 | 4/1994 |

* cited by examiner

*Primary Examiner*—John P. Leubecker
(74) *Attorney, Agent, or Firm*—Greenblum & Bernstein, P.L.C.

(57) ABSTRACT

A self-retaining endoscope includes an observation base portion which can be inserted into a body cavity through a mouth of a patient to be examined and which is provided with an objective optical system and an illumination window, and a flexible catheter portion which is provided with an image transmission system for transmitting an image formed by the objective optical system and a light transmission system for causing the illumination window to emit illumination light and which can be inserted into the body through a nasal cavity of the patient. The catheter portion is connected to the observation base portion. An external device is detachably attached to a distal end of the catheter portion and has a monitor portion adapted to view the image through the image transmission system and a lighting device which provides light energy to the light transmission system.

14 Claims, 7 Drawing Sheets

SELF-RETAINING ENDOSCOPE

BACKGROUND OF THE INVENTION

1. Field of the Invention

The present invention relates to a self-retaining endoscope which can relieve a patient to be examined from pain even if the endoscope is retained in the patient's body for long time.

2. Description of the Related Art

In an endoscopy examination, in general, an endoscope has a body insertion portion and an operation portion connected thereto via a flexible tube. The body insertion portion is introduced into a patient's body through his or her mouth to view a target inner part of the body. The body insertion portion of the endoscope must be sometimes inserted and retained in the body for a long time to observe the progress of a diseased part within the body or obtain and/or record somatoscopic information of a patient under ordinary every-day living conditions. However, the insertion and retainment of the endoscope in the body through the patient's mouth causes the patient to suffer from significant pain.

To relieve the pain from the patient, it is known to use a capsule type endoscope which is provided at an intermediate portion of a flexible continuous member, as disclosed in Japanese Unexamined Patent Publication No. 64-76822. A patient to be examined swallows a soft ball formed at a tip end of the flexible continuous member in the evening of the day before an examination, so that the soft ball will be discharged from the patient's anus the next day. An operator pulls or moves the tip end and the tail end of the flexible continuous member to thereby move or guide the capsule connected to the intermediate portion of the flexible continuous member.

In the endoscope which is in the form of a capsule as mentioned above, the pain that the patient suffers can be eased in comparison with conventional endoscopes. However, the patient must always carry the flexible continuous member whose one end extends out of his or her mouth for more than 12 hours. Consequently, it is impossible for the patient to take a meal or speak. Under these circumstances, no substantial pain relieving effect can be expected. Moreover, it is difficult to control the position of the endoscope in the form of a capsule.

SUMMARY OF THE INVENTION

It is an object of the present invention to provide a self-retaining endoscope which can relieve a patient to be examined from pain.

To achieve the object mentioned above, according to the present invention, a self-retaining endoscope is provided which includes an observation base portion adapted to be inserted into a body cavity through a mouth of a patient to be examined, the observation base portion being provided with an objective optical system and an illumination window; a catheter portion connected to the observation base portion, adapted to be inserted from inside the body of the patient through a nasal cavity of the patient, the catheter portion including an image transmission system for transmitting an image formed by the objective optical system and a light transmission system for causing the illumination window to emit illumination light; and an external device adapted to be detachably attached to a distal end of the catheter portion, the external device including a monitor portion adapted to view the image through the image transmission system, and a lighting device which provides light energy to the light transmission system.

Preferably, the observation base portion is provided with a bending portion, the catheter portion is provided therein with bending operation wires, and the external device includes a bending device which operates the bending operation wires to bend the bending portion.

Preferably, the bending operation wires are made of a shape memory alloy, and the self-retaining endoscope further includes a power supply/heat selection device for selectively heating the bending operation wires to bend the bending portion.

Preferably, the observation base portion includes a rigid portion having an objective optical system and an illumination window, a bending portion which is bendable, and a flexible portion which is deformed when an external force is applied thereto, in this order from the front end of the observation base portion.

In an embodiment, the light transmission system is a light guide fiber, and the lighting device is a light source.

In an embodiment, the illumination window is provided with an LED, wherein the light transmission system and the lighting device are a power supply line and a power supply, respectively.

In an embodiment, the image transmission system is an image guide fiber.

In an embodiment, the objective optical system includes a CCD and the image transmission system is a signal line.

Preferably, the observation base portion is provided with an endoscope element (such as an air supply port), and the catheter portion is provided therein with a supply tube connected at the front end thereof to the endoscope element; wherein the external device is provided with an endoscope element actuating device, which is detachably attached to the distal end of the supply tube, for utilizing the endoscope element.

In an embodiment, the endoscope element is an air supply port, the supply tube is an air supply tube, and the endoscope element actuating device is an air supplier.

In an embodiment, the endoscope element is an air supply port and a water supply port, the supply tube is an air supply tube and a water supply tube, and the endoscope element actuating device is an air supplier and a water supplier.

According to another aspect of the present invention, a self-retaining endoscope includes an observation base portion adapted to be inserted into a body cavity through a mouth of a patient to be examined; a catheter portion connected to the observation base portion, adapted to be inserted from inside the body of the patient through a nasal cavity of the patient; and an external device adapted to be detachably attached to a distal end of the catheter portion.

The external device is connected to the distal end of the catheter portion after the catheter portion is inserted through the nasal cavity of the patient. The observation base portion is provided with an objective optical system and an illumination window. The external device is provided with a monitor portion and a lighting device. The catheter portion is provided with an image transmission system for transmitting an image formed by the objective optical system to the monitor portion, and a light transmission system for transmitting a light from the lighting device to the illumination window.

The present disclosure relates to subject matter contained in Japanese Patent Application No. 11-104795 (filed on Apr.

13, 1999) which is expressly incorporated herein by reference in its entirety.

BRIEF DESCRIPTION OF THE DRAWINGS

The invention will be discussed below in detail with reference to the drawings, in which.

DESCRIPTION OF THE PREFERRED EMBODIMENT

FIGS. 1, 2 and 5 through 14 show a first embodiment of a self-retaining endoscope according to the present invention. The endoscope includes a base portion 10, a catheter portion 11, and an external device 12, in this order from the distal end. The base portion 10 includes a rigid portion 10A, a bending portion 10B and a flexible portion 10C, in this order from the distal end. The catheter portion 11 is secured to the rear end of the flexible portion 10C. The rigid portion 10A is made of, for example, plastic which is not macroscopically deformable.

Figure 1:
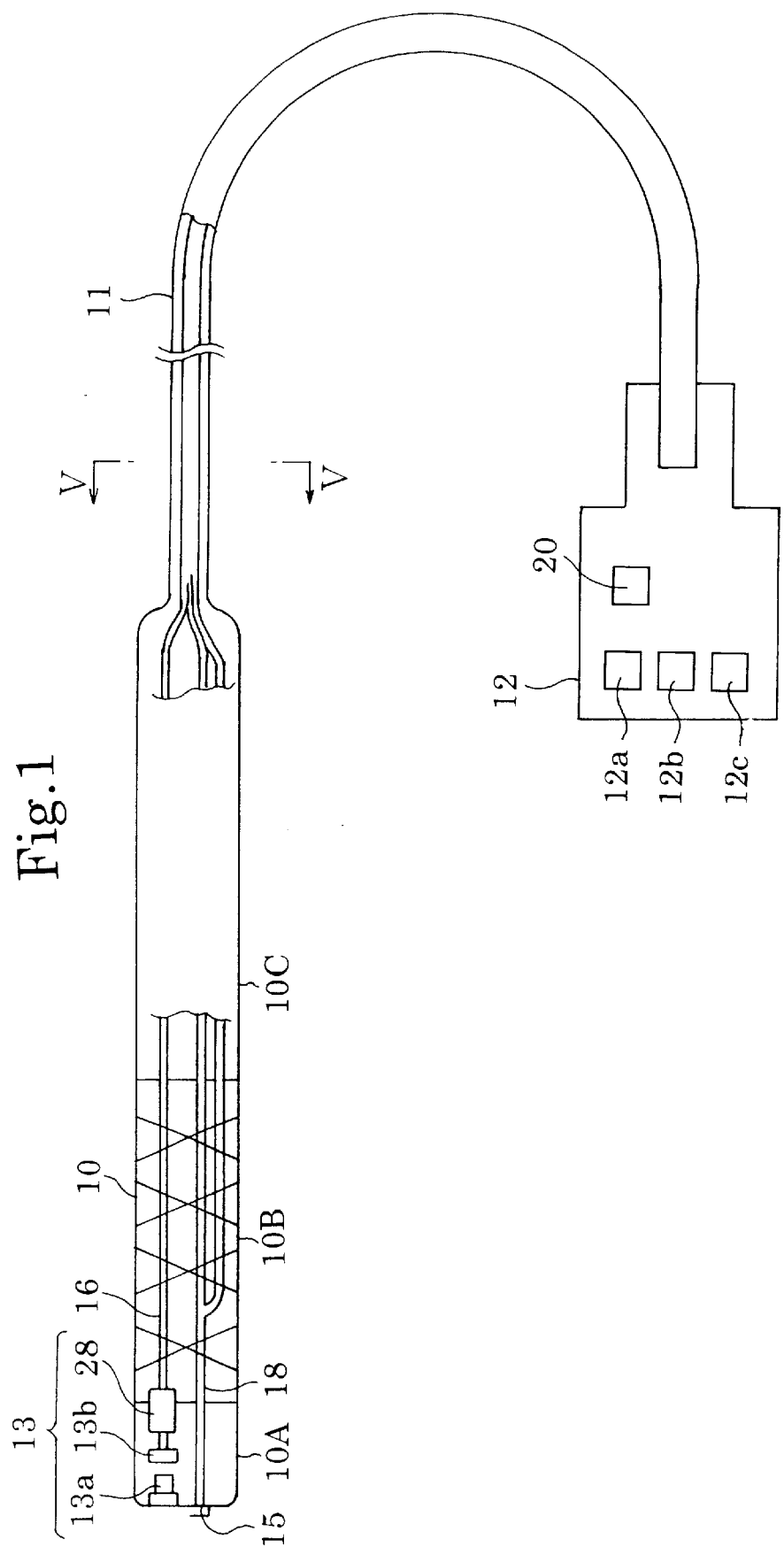
FIG. 1 is a partially sectioned schematic view of a self-retaining endoscope according to an embodiment of the present invention.

The flexible portion 10C is bendable or deformable along the shape of a digestive tract when it is inserted in the body cavity. The bending portion 10B is made of, for example, a metal net, and is more flexible than the flexible portion 10C, so that the base portion can be bent at the flexible portion 10C. The catheter portion 11 is detachably attached to the external device 12. In FIG. 1, the catheter portion 11 is connected to the external device 12.

The flexibility and the diameter of the catheter portion 11 are such that it can be inserted into the body through a nasal cavity. Accordingly, the outer diameter of the catheter portion 11 is preferably not greater than 8 mm and is more preferably equal to or smaller than 6 mm.

The rigid portion 10A of the base portion 10 is provided with an objective optical system 13, an illumination window 14, and an element such as an air supply port 15. The objective optical system 13 includes an objective lens 13a, a CCD 13b, and an amplifier circuit 28 which is connected to a signal line or other image transmission system 16. The signal line 16 extends within the base portion 10 and the catheter portion 11 and projects out of the end of the catheter portion 11. The projection end of the signal line 16 is connected to a monitor 12a provided in the external device 12.

Figure 2:
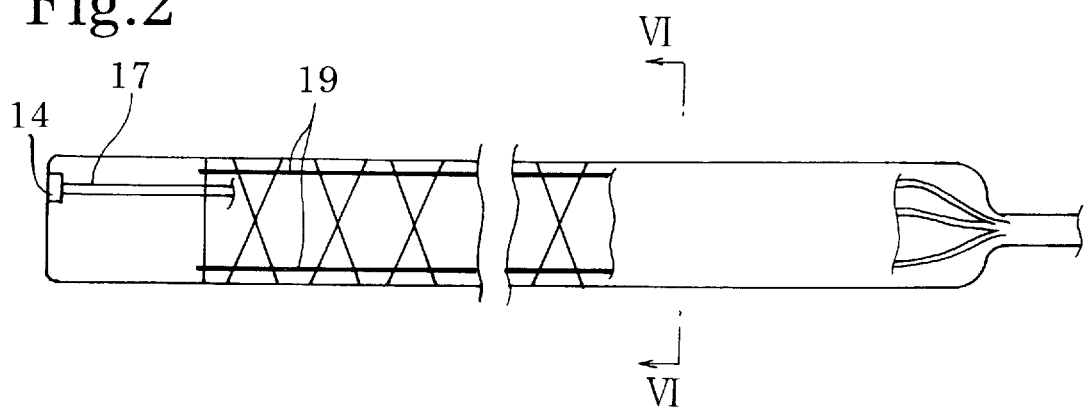
FIG. 2 is another sectional view of a part of a self-retaining endoscope shown in FIG. 1.

As shown in FIG. 2, a light guide fiber or other light transmission system 17 is opened at its distal end into the illumination window 14. The light guide fiber 17 extends in the base portion 10 and the catheter portion 11 and projects from the end of the catheter portion 11. The projection end of the light guide fiber 17 is connected to a light source 12b or other lighting device provided in the external device 12.

The air supply port 15 is connected to an air supply tube 18 which extends within the base portion 10 and the catheter portion 11. The air supply tube 18 protrudes from the end of the catheter portion 11. The projection end of the air supply tube 18 is connected to an air supplier 12c or other endoscope element actuating device provided in the external device 12, so that air can be supplied through the air supply port 15 to expand the cavity. Consequently, the distance between the base portion 10 and the inner wall of the digestive tract can be increased, so that the observation by a viewer can be facilitated.

Figure 6:
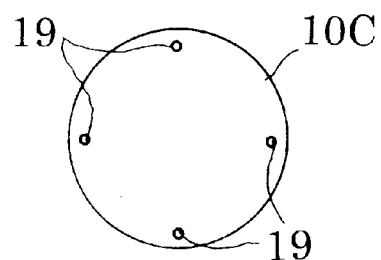
FIG. 6 is a sectional view taken along the line VI—VI in FIG. 2.

The base portion 10 and the catheter portion 11 are provided therein with a plurality of bendable operation wires (four wires in the illustrated embodiment) 19 extending therethrough (FIG. 6). The operation wires 19 are each secured at the front ends thereof to the rigid portion 10A and extend from the bending portion 10B to the flexible portion 10C and the catheter portion 11. As is well known in the art, when any operation wire 19 is pulled, the bending portion 10B is bent so that the diameter of the portion corresponding to the pulled operation wire is reduced. The operation wires 19 project from the rear end of the catheter portion 11 and are connected to the bending device 20 of the external device 12.

Figure 8:
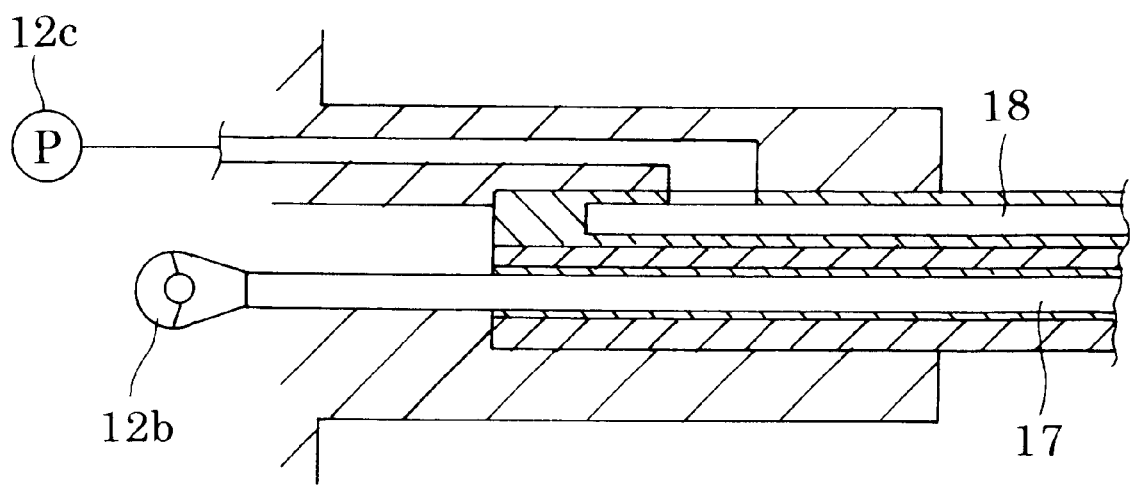
FIG. 8 is a sectional view of a connection between a catheter portion and an external device.

The catheter portion 11 connected to the external device 12 is shown in section in FIG. 8. When the catheter portion 11 is mounted to the external device 12, the light guide fiber 17 and the air supply tube 18 are connected to the light source 12b and the air supplier 12c, respectively. Consequently, illumination light can be emitted from the illumination window 14, and air can be supplied to the air supply port 15. The signal line 16 is connected to the monitor 12a, so that an object image formed by the objective optical system 13 can be viewed on the monitor 12a.

Figure 9:
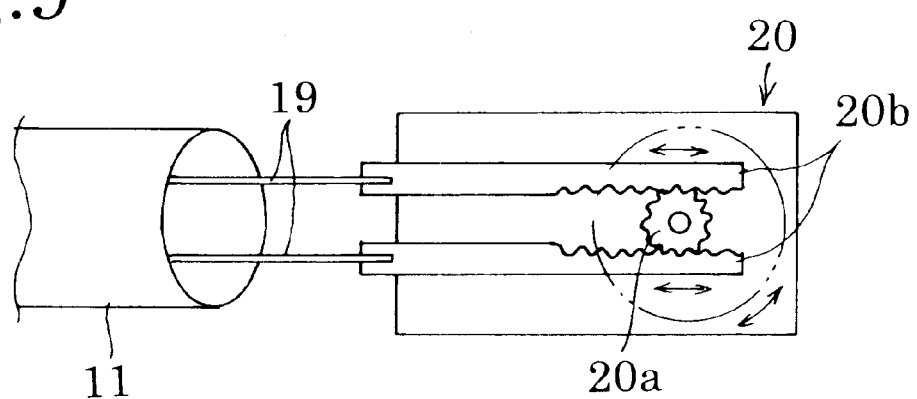
FIG. 9 is an explanatory view of a bending mechanism.
Figure 10:
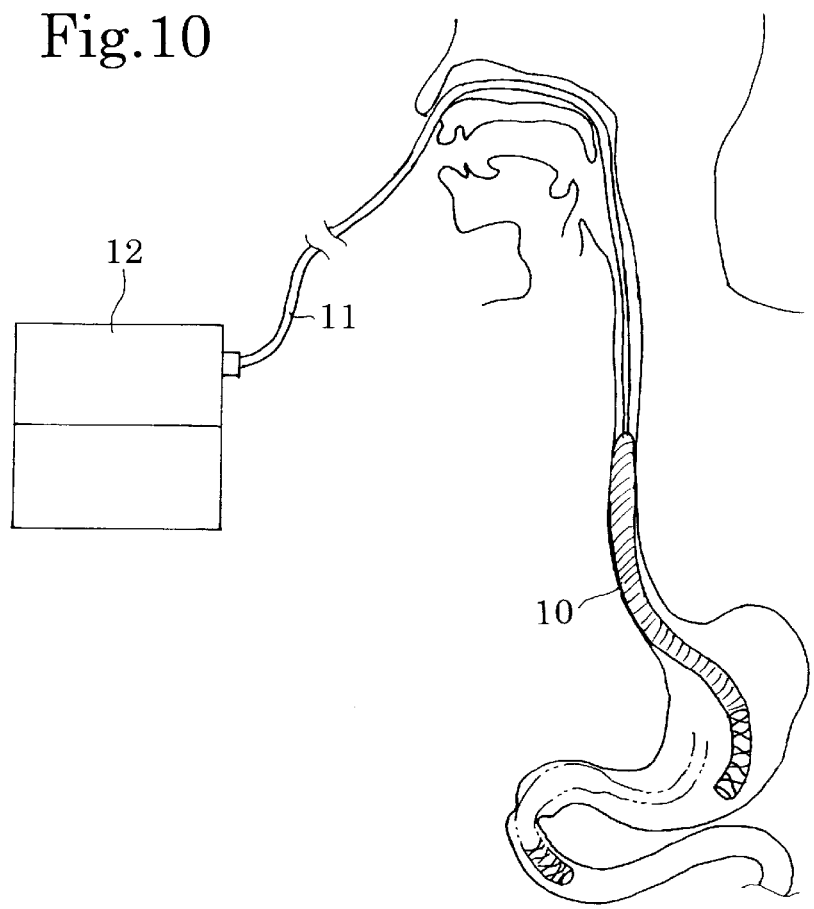
FIG. 10 is a schematic view of an endoscope retained in a body and connected to an external device, according to the present invention.
Figure 11:
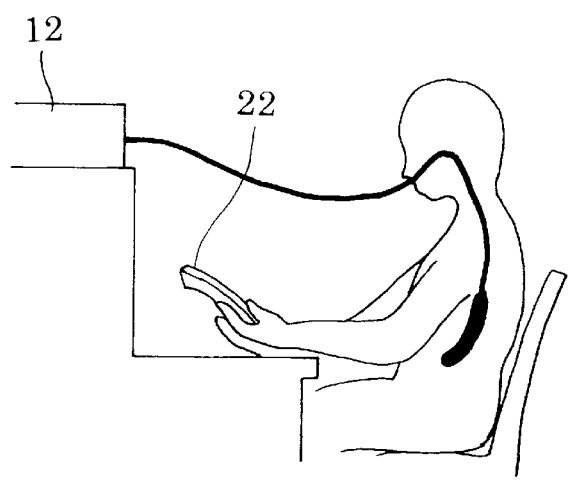
FIG. 11 is a schematic view of an endoscope retained in a body under ordinary every-day living conditions, according to the present invention.

The four operation wires 19 are secured at the front ends thereof to the rigid portion 10A at an angular distance of 90 degrees in orthogonal directions of the cylindrical base portion 10. The two diametrically opposed operation wires 19 are connected, at the projection ends thereof projecting from the catheter portion 11, to respective racks 20b of the bending device 20, as shown in FIG. 9. A pair of racks 20b are in mesh with a common pinion 20a, so that when the rotation of the pinion 20a takes place, the racks 20b are moved in mutually opposite directions. Consequently, one of a pair of operation wires connected to the racks 20b is pulled and the other operation wire is pushed. Namely, the bending portion is bent by rotating the pinion 20a. Although only two operation wires 19 are shown in FIG. 9, the same is true for the remaining two operation wires 19. Note that if it is necessary for the bending portion 10B to be bent in only one direction, only two operation wires 19 are necessary.

Figure 12:
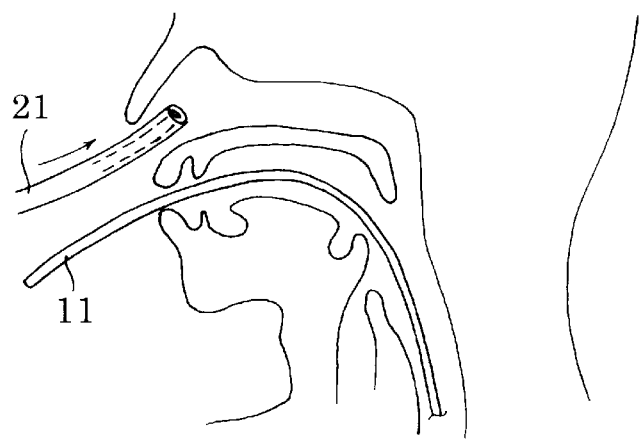
FIG. 12 is a schematic view showing a step in an insertion process of a distal end of a catheter portion into a nasal cavity.
Figure 13:
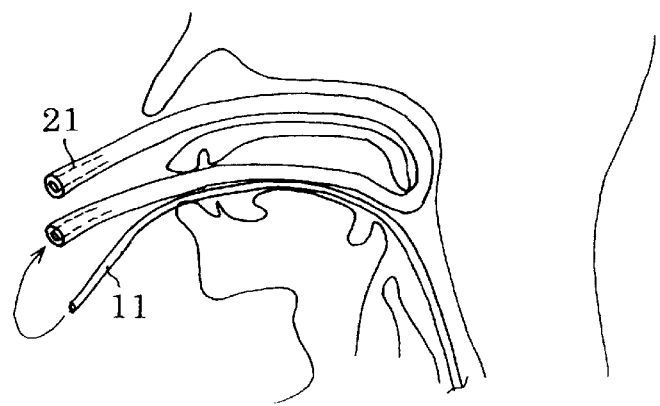
FIG. 13 is a schematic view showing a step in an insertion process of a distal end of a catheter portion into a nasal cavity.
Figure 14:
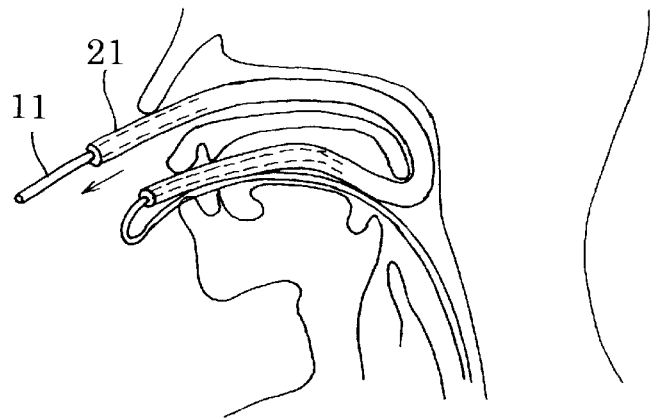
FIG. 14 is a schematic view showing a step in an insertion process of a distal end of a catheter portion into a nasal cavity.

In the endoscope constructed as above, when the catheter portion 11 is detached from the external device 12, a patient to be examined swallows the base portion 10 via his or her mouth. Consequently, the catheter portion 11 secured to the rear end of the base portion 10 extends out of the mouth (FIG. 12). An introduction tube 21 is inserted in the body through the nasal cavity so that the leading end of the introduction tube 21 extends outward from the mouth (FIG. 13). In this state, the distal end of the catheter portion 11 extending outward from the mouth is inserted in the introduction tube 21 that extends outward from the mouth, to the portion of the introduction tube 21 within the nasal cavity (FIG. 14). The introduction tube 21 is removed from the nasal cavity, so that the distal end of the catheter portion 11 extends outward from the nasal cavity. Then the catheter portion 11 is connected to the external device 12, so that an operator can view the inner part of the body through the endoscope.

Namely, illumination light is supplied to the illumination window 14 of the base portion 10 through the light guide fiber 17. The object image upon which the illumination light is impinged is formed on an image pickup surface of the CCD 13b through the objective lens 13a. The image signal supplied from the CCD 13b is amplified by the amplifier circuit 28, so that the image can be viewed on the monitor 12a of the external device 12 through the signal line 16. An operator actuates the bending device 20 to bend the bending portion 10B to thereby change the direction of the objective lens 13a in order to observe the target inner part of the body.

When observation or treatment using the endoscope is not required, the catheter portion 11 is disconnected from the external device 12. Consequently, the patient who is subject to an examination is free from pain and can carry out usual daily activities. Moreover, even when the catheter portion 11 is connected to the external device 12 the patient can, for example, freely read a book 22 since the catheter portion 11 extends in the nasal cavity.

If the extending portion of the catheter portion 11 from the nasal cavity is not secured, the swallowed base portion 10 gradually moves down the digestive tract due to peristalsis. Therefore, when the base portion 10 reaches the target part of the body, the distal end of the catheter portion 11 extending out of the body is connected to the external device 12 to conduct an observation or other treatments. If the extending portion of the catheter portion 11 is immovably fixed at a desired position to stop the movement of the base portion 10 due to the peristalsis, the base portion 10 can be retained at a desired position.

Figure 3:
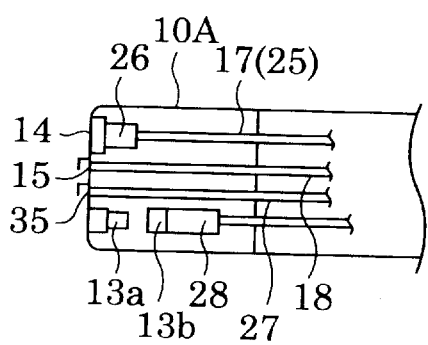
FIG. 3 is a partially broken schematic view of a self-retaining endoscope according to another embodiment of the present invention.
Figure 15:
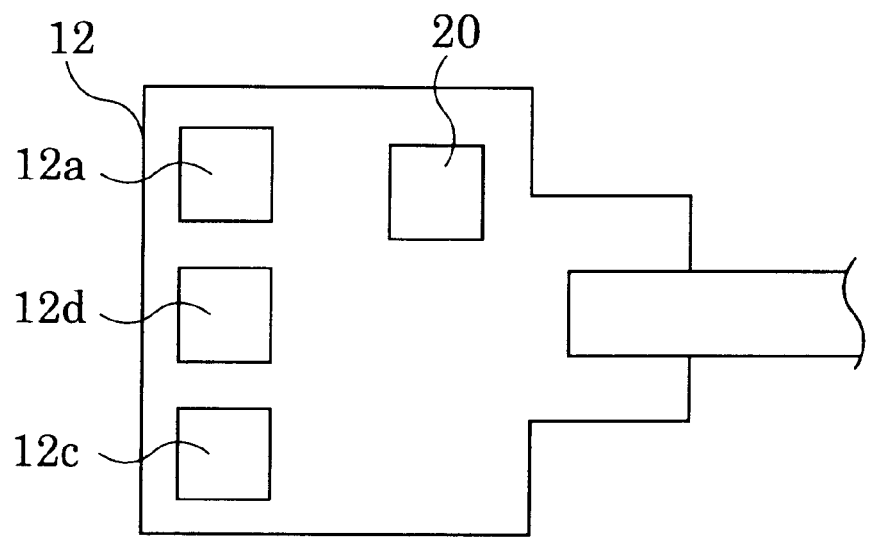
FIG. 15 is a schematic view showing an external device of a self-retaining endoscope according to another embodiment of the present invention.

FIG. 3 shows another embodiment of an endoscope according to the present invention. In this embodiment, an LED 26 is secured to the illumination window 14, and a power supply line 25 is used as the light transmission system 17. The power is supplied to the LED 26 by a power supply 12d provided in the external device 12, so that the light can be emitted from the illumination window 14. In this embodiment, the light source 12b of above-described embodiment is replaced by the power supply 12d (see FIG. 15).

Figure 4:
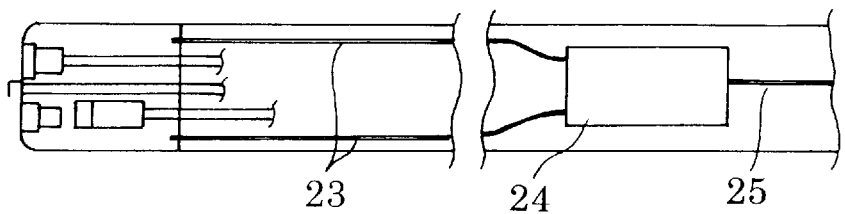
FIG. 4 is a partially broken schematic view of a self-retaining endoscope according to another embodiment of the present invention.

FIG. 4 shows another embodiment of an endoscope according to the present invention. In this embodiment, the bending wires 23 are each made of an SMA (shape memory alloy), and a power supply and heat selection circuit (power supply/heat selection device) 24 is provided in the flexible portion 10C to selectively supply and heat the bending wires 23 with electrical power. The power supply and heat selection circuit 24 is connected to the external device 12 through the power supply line 25 extending in the catheter portion 11. Bending can be carried out by selectively supplying the power to the bending wires 23 to heat the same through the external device 12.

Figure 5:
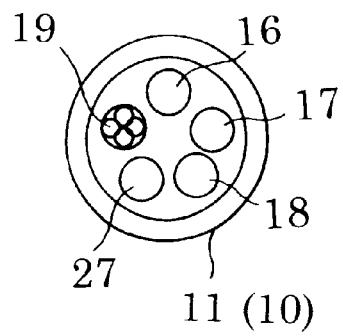
FIG. 5 is a sectional view taken along the line V—V in FIG. 1.
Figure 7:
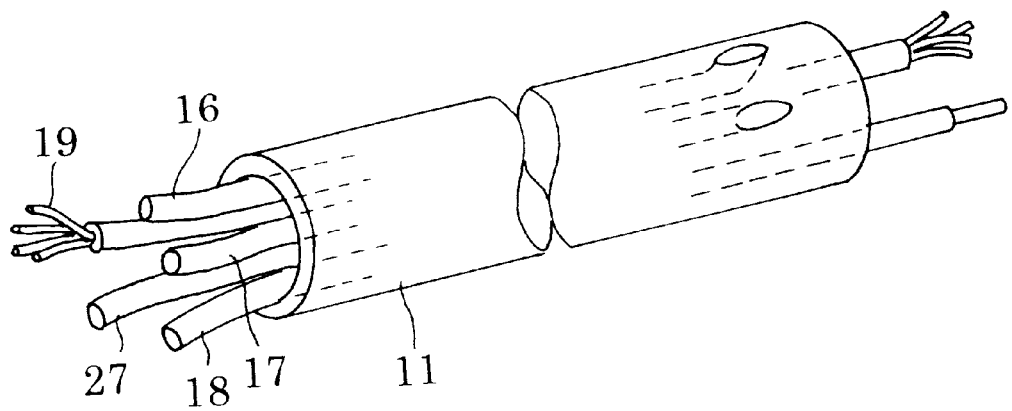
FIG. 7 is a partially broken perspective view of a catheter portion.
Figure 16:
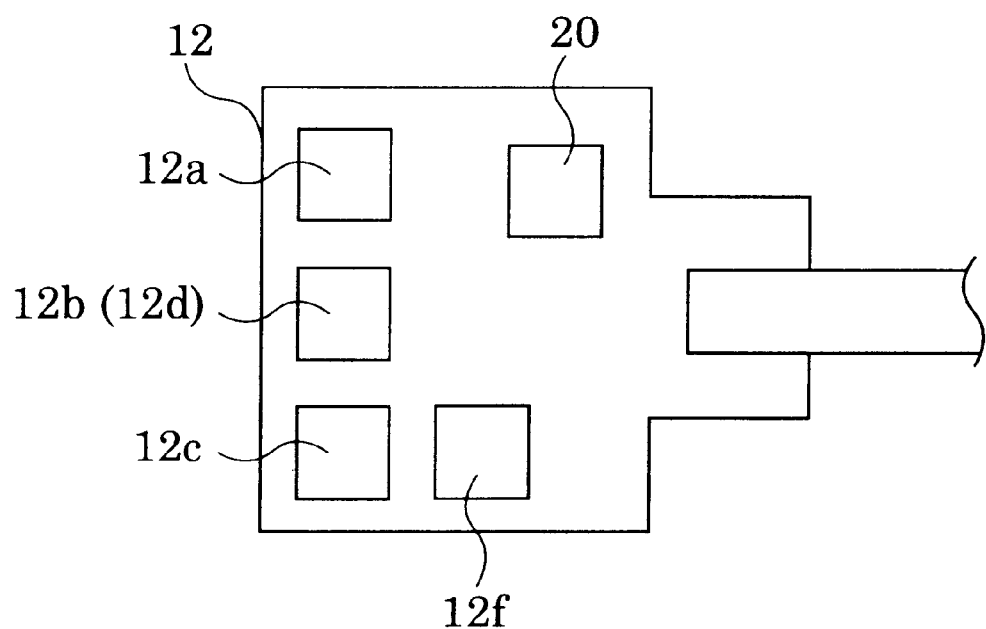
FIG. 16 is a schematic view showing an external device of a self-retaining endoscope according to another embodiment of the present invention.

In the catheter portion 11 (and in the base portion 10), it is possible to arrange not only the air supply tube 18 but also a water supply tube 27 as shown in FIGS. 3, 5 and 7. In this case, the water supply tube 27 is connected (at the front end thereof) to a water supply port 35 which is provided in the rigid portion 10A of the base portion 10, as shown in FIG. 3. The water supply tube 27 is connected at the distal end thereof to a water supplier 12f, as shown in FIG. 16. In addition, or as an alternative, a treatment tool insertion tube can be provided in the catheter portion 11.

Examples of the connection of various elements provided on the external device 12 (e.g., the monitor 12a, the light source 12b, the air supplier 12c, the power supply 12d, and the water supplier 12f) to the base portion 10, in the above-described embodiments, are disclosed in Japanese Patent No. 2750146, and in Japanese Patent Publication No. Sho-64-4450.

As can be understood from the above discussion, according to the present invention, since the base portion retained in the body cavity and the external device 12 are interconnected by the catheter portion which can be inserted in the body cavity through the nasal cavity, a patient to be examined suffers from no pain even if it takes long time to view an inner part of the body.

Obvious changes may be made in the specific embodiments of the present invention described herein, such modifications being within the spirit and scope of the invention claimed. It is indicated that all matter contained herein is illustrative and does not limit the scope of the present invention.

What is claimed is:

1. A self-retaining endoscope comprising:
an observation base portion configured to be inserted into a body cavity through a mouth of a patient to be examined, said observation base portion being provided with an objective optical system and an illumination window;
a catheter portion connected to the observation base portion, configured to be inserted from inside the body of the patient through a nasal cavity of the patient, said catheter portion including an image transmission system for transmitting an image formed by the objective optical system and a light transmission system for causing the illumination window to emit illumination light, wherein the diameter of a proximal end of said catheter portion is substantially the same as the diameter of a remaining length of said catheter portion; and
an external device configured to be detachably attached to said proximal end of the catheter portion, said external device including a monitor portion adapted to view the image through the image transmission system, and a lighting device which provides light energy to the light transmission system.

2. The self-retaining endoscope according to claim 1, wherein said observation base portion is provided with a bending portion; said catheter portion being provided therein with bending operation wires; and said external device including a bending device which operates said bending operation wires to bend said bending portion.

3. The self-retaining endoscope according to claim 2, wherein said bending operation wires are made of a shape memory alloy, and wherein said self-retaining endoscope further includes a power supply/heat selection device for selectively heating said bending operation wires to bend the bending portion.

4. The self-retaining endoscope according to claim 2, wherein said observation base portion comprises a rigid portion having an objective optical system and an illumination window and a flexible portion which is deformed when an external force is applied thereto, in this order from the front end of the observation base portion.

5. The self-retaining endoscope according to claim 1, wherein said light transmission system comprises a light guide fiber, and wherein said lighting device includes a light source.

6. The self-retaining endoscope according to claim 1, wherein said illumination window is provided with an LED and wherein said light transmission system and said lighting device includes a power supply line and a power supply, respectively.

7. The self-retaining endoscope according to claim 1, wherein said image transmission system comprises an image guide fiber.

8. The self-retaining endoscope according to claim 1, wherein said objective optical system comprises a CCD and wherein said image transmission system includes a signal line.

9. The self-retaining endoscope according to claim 1,
wherein said observation base portion base portion is provided with an endoscope element, and said catheter portion is provided therein with a supply tube connected, at the front end thereof, to said endoscope element; and
wherein said external device is provided with an endoscope element actuating device, which is detachably attached to the proximal end of said supply tube, for utilizing said endoscope element.

10. The self-retaining endoscope according to claim 9, wherein said endoscope element comprises an air supply port, said supply tube comprises an air supply tube, and said endoscope element actuating device includes an air supplier.

11. The self-retaining endoscope according to claim 9, wherein said endoscope element comprises an air supply port and a water supply port, said supply tube includes an air supply tube and a water supply tube, and said endoscope element actuating device includes an air supplier and a water supplier.

12. A self-retaining endoscope comprising:
an observation base portion configured to be inserted into a body cavity through a mouth of a patient to be examined;
a catheter portion connected to the observation base portion, configured to be inserted from inside the body of the patient through a nasal cavity of the patient, wherein the diameter of a proximal end of said catheter portion is substantially the same as the diameter of a remaining length of said catheter portion; and
an external device adapted to be detachably attached to said proximal end of the catheter portion, said external device being connected to the proximal end of the catheter portion after the catheter portion is inserted through the nasal cavity of the patient;
wherein said observation base portion is provided with an objective optical system and an illumination window;
wherein said external device is provided with a monitor portion and a lighting device; and
wherein said catheter portion is provided with an image transmission system for transmitting an image formed by the objective optical system to the monitor portion and a light transmission system for transmitting a light from the lighting device to the illumination window.

13. The self-retaining endoscope according to claim 4, a diameter of said catheter portion being smaller than a diameter of said flexible portion.

14. A self-retaining endoscope comprising:
an observation base portion configured to be inserted into a body cavity through a mouth of a patient to be examined, said observation base portion being provided with an objective optical system and an illumination window, said observation base portion comprising an endoscope element;
a catheter portion connected to the observation base portion, configured to be inserted from inside the body of the patient through a nasal cavity of the patient, said catheter portion including an image transmission system for transmitting an image formed by the objective optical system and a light transmission system for causing the illumination window to emit illumination light, wherein the diameter of a proximal end of said catheter portion is substantially the same as the diameter of a remaining length of said catheter portion, said catheter portion comprising a supply tube connected, at the front end thereof, to said endoscope element; and
an external device configured to be detachably attached to said proximal end of the catheter portion, said external device including a monitor portion configured to view the image through the image transmission system, and a lighting device which provides light energy to the light transmission system, said external device comprising an endoscope element actuating device, which is detachably attached to the distal end of said supply tube, for actuating said endoscope element;
wherein a diameter of said catheter portion is smaller than a diameter of a flexible portion of said observation base portion.

* * * * *